United States Patent
Greiner-Perth et al.

(10) Patent No.: US 9,101,730 B2
(45) Date of Patent: Aug. 11, 2015

(54) DISCHARGING DEVICE FOR LIQUID MEDIA

(75) Inventors: Juergen Greiner-Perth, Gottmadingen (DE); Joerg Bieg, St. Georgen (DE)

(73) Assignee: APTAR RADOLFZELL GMBH, Radolfzell (DE)

( * ) Notice: Subject to any disclaimer, the term of this patent is extended or adjusted under 35 U.S.C. 154(b) by 724 days.

(21) Appl. No.: 13/387,602

(22) PCT Filed: Jul. 23, 2010

(86) PCT No.: PCT/EP2010/004516
§ 371 (c)(1),
(2), (4) Date: Jan. 27, 2012

(87) PCT Pub. No.: WO2011/015292
PCT Pub. Date: Feb. 10, 2011

(65) Prior Publication Data
US 2012/0126035 A1    May 24, 2012

(30) Foreign Application Priority Data

Aug. 3, 2009   (DE) .......................... 10 2009 037 164

(51) Int. Cl.
*B05B 1/34*    (2006.01)
*A61M 15/08*   (2006.01)
(Continued)

(52) U.S. Cl.
CPC ............... *A61M 15/08* (2013.01); *A61M 11/00* (2013.01); *A61M 11/007* (2014.02);
(Continued)

(58) Field of Classification Search
CPC .............. A61M 15/08; A61M 11/007; A61M 2205/11; A61M 2210/0618; B05B 11/307; B05B 1/3421; B05B 1/3436

USPC .............. 239/329, 333, 487, 494; 222/321.1, 222/321.4, 321.6, 321.7, 325, 378
See application file for complete search history.

(56) References Cited

U.S. PATENT DOCUMENTS 3,949,939 A    4/1976 Brown
5,813,570 A    9/1998 Fuchs et al.
(Continued)

FOREIGN PATENT DOCUMENTS

DE    26 04 001 A1    5/1977
DE    197 00 437 A1   7/1997
(Continued)

OTHER PUBLICATIONS

Office Action of Russian Patent Office dated May 20, 2014 issued in Application No. 2012105333/14 with English translation (11 pages).
(Continued)

*Primary Examiner* — Dinh Q Nguyen
(74) *Attorney, Agent, or Firm* — Flynn, Thiel, Boutell & Tanis, P.C.

(57) ABSTRACT

Discharging unit for discharging pharmaceutical media from a medium storage receptacle, including a first discharge orifice, a pump, an inlet duct connecting the medium storage receptacle to the pump, and an outlet duct for connecting the pump to the first discharge orifice. The first discharge orifice is part of a first subordinate device of the discharging unit and the pump, a portion of the outlet duct, and an outlet valve provided in the outlet duct are part of a second subordinate device of the discharging unit. The first subordinate device is capable, without the use of tools, of being coupled to, and decoupled from, the second subordinate device, and an internal volume of a portion of the outlet duct extending from the outlet valve to the first discharge orifice is less than 15 μl.

23 Claims, 2 Drawing Sheets

(51) Int. Cl.
*A61M 11/00* (2006.01)
*B05B 11/00* (2006.01)

(52) U.S. Cl.
CPC .......... *B05B 11/3001* (2013.01); *B05B 11/307* (2013.01); *A61M 2205/11* (2013.01); *A61M 2206/16* (2013.01); *A61M 2210/0618* (2013.01); *B05B 1/3421* (2013.01); *B05B 1/3436* (2013.01)

(56) References Cited

U.S. PATENT DOCUMENTS

| | | | |
|---|---|---|---|
| 5,944,222 | A | 8/1999 | Fuchs et al. |
| 5,950,877 | A | 9/1999 | Garcia et al. |
| 6,059,150 | A | 5/2000 | Fuchs et al. |
| 6,059,151 | A * | 5/2000 | Fuchs ................. 222/321.6 |
| 6,269,976 | B1 | 8/2001 | DeJonge |
| 6,321,942 | B1 | 11/2001 | Krampen et al. |
| 6,578,741 | B2 | 6/2003 | Ritsche et al. |
| 7,717,299 | B2 | 5/2010 | Greiner-Perth |
| 7,726,522 | B2 | 6/2010 | Greiner-Perth |
| 7,828,231 | B2 | 11/2010 | Harms |
| 2002/0011530 | A1* | 1/2002 | Fuchs ........................ 239/333 |
| 2002/0066752 | A1 | 6/2002 | Ritsche et al. |
| 2006/0011659 | A1 | 1/2006 | Greiner-Perth et al. |
| 2006/0011663 | A1 | 1/2006 | Greiner-Perth |
| 2006/0016833 | A1 | 1/2006 | Greiner-Perth |
| 2006/0186141 | A1 | 8/2006 | Greiner-Perth |
| 2008/0230633 | A1 | 9/2008 | Harms |
| 2009/0026289 | A1 | 1/2009 | Nadler et al. |
| 2009/0236445 | A1 | 9/2009 | Lintern et al. |
| 2009/0255959 | A1* | 10/2009 | Pruvot ..................... 222/321.6 |

FOREIGN PATENT DOCUMENTS

| | | |
|---|---|---|
| DE | 100 23 551 A1 | 12/2001 |
| DE | 10 2005 033 771 A1 | 1/2007 |
| EP | 0 818 247 A1 | 1/1998 |
| EP | 1 199 107 A2 | 4/2002 |
| EP | 1 616 631 A2 | 1/2006 |
| FR | 2 736 285 | 1/1997 |
| FR | 2 738 553 | 3/1997 |
| GB | 1 517 642 A | 7/1978 |
| RU | 62524 (U1) | 4/2007 |
| WO | WO 03/078073 A1 | 9/2003 |
| WO | WO 2007/096049 A2 | 8/2007 |
| WO | WO 2007/138084 A2 | 12/2007 |

OTHER PUBLICATIONS

Form PCT/IB/338 Notification of Transmittal of Translation of International Preliminary Report on Patentability mailed Feb. 16, 2012 (1 page).
Form PCT/IB/373 International Preliminary Report on Patentability issued Feb. 7, 2012 (1 page).
Form PCT/ISA/237 Translation of PCT Written Opinion of the International Searching Authority (20 pages).
Form PCT/ISA/220 mailed May 3, 2011 (1 page).
Form PCT/ISA/237 mailed May 3, 2011 (14 pages).
Form PCT/ISA/210 mailed May 3, 2011 with English translation (15 pages).
German Patent Office Examination Report dated Jun. 15, 2010 (2 pages).

* cited by examiner

DISCHARGING DEVICE FOR LIQUID MEDIA

FIELD OF APPLICATION AND PRIOR ART

The invention relates to a discharging unit for discharging pharmaceutical media from a medium storage receptacle, which discharging unit comprises a first discharge orifice, a pump, an inlet duct for connecting the medium storage receptacle to the pump, and an outlet duct for connecting the pump to the first discharge orifice.

Generic discharging units are well known in the prior art. They are usually connected to a medium storage receptacle which is either accommodated in the housing of the discharging unit or onto which the discharging unit is fitted. Medium can then be pumped from the medium storage receptacle to the discharge orifice, whence it is dispensed to the environment usually in a nebulized form. In particular, generic discharging units can be in the form of nasal dispensers. As such, they comprise a nasal tube which is intended for insertion into a nostril of a patient and on which the first discharge orifice is provided.

If a discharging unit is used by only one patient, then it is naturally not necessary to take measures to prevent the patient from being contaminated by another patient using the same discharging unit. It becomes problematic when a generic discharging unit is used on a number of patients in conjunction with an inoculant, for example, since this usage involves the risk of pathogenic organisms on one patient remaining on the discharging unit after it has been used by said patient and of an infection being caused in a patient subsequently using the discharging unit.

It is feasible, when using a conventional generic discharging unit, to replace the discharge head comprising the nasal tube before the latter is used by a subsequent patient. However, such replacement results at the same time in a significant loss of pharmaceutical medium, since the discharge head of prior generic discharging units includes a significant portion of the discharge duct. Additionally, such a replacement of the discharge head makes it then necessary to first completely refill the discharge duct with medium, in order to achieve the planned dosage. Therefore, it would be necessary to first carry out so-called priming of the discharging unit following replacement of the discharge head of prior generic discharging units, that is to say, it would be necessary to execute some pumping strokes in order to fill the entire discharge duct with medium before operating the discharging unit. Here again, a significant portion of pharmaceutical medium would be lost.

While in many kinds of applications it is merely regrettable when pharmaceutical medium is lost, the loss of a significant amount of the active ingredient in the aforementioned manner is inacceptable in the case of mass inoculations performed during pandemics due to the limited availability of the active ingredient in most cases.

A problem that likewise occurs in conjunction with mass inoculations is that these necessitate the provision of large quantities of discharging units within a very short period of time for the purpose of discharging a pharmaceutical medium. In this case, there may not always be sufficient time to produce such large quantities of discharging units. The precautionary storage of a large number of discharging units is not a satisfactory solution, since the connecting unit usually provided on generic discharging units for connecting the same to a medium storage receptacle must be adapted to suit the respective type of medium storage receptacle. The resulting lack of flexibility in the use of the discharging unit is likewise regarded as not being advantageous.

OBJECT AND ITS ACHIEVEMENT

It is therefore an object of the invention to develop and supplement a generic discharging unit to the extent that it is suitable, in particular, for use on several patients and/or with different types of medium storage receptacles.

As regards the usability of a generic discharging unit by several patients whilst at the same time avoiding any so-called cross-contamination, the basic concept of the present invention relates to the design of that part of the discharging unit that is always used for only one patient at any given time such that only a small amount of the pharmaceutical medium is lost when said part of the discharging unit is replaced. In order to make it possible to use the discharging unit in immediate succession for two patients without interim priming thereof, provision is made to the effect that not more than 15 μl of the medium will be lost during the replacement of the components concerned.

In a first concept of the invention, the first discharge orifice is part of a first subordinate device of the discharging unit. The pump, at least a portion of the outlet duct, and an outlet valve provided in the outlet duct are part of a second subordinate device of the discharging unit. The first subordinate device is one that can be coupled to the second subordinate device and likewise decoupled from the same without the use of tools. Furthermore, an internal volume of a portion of the outlet duct that extends from the outlet valve to the first discharge orifice is less than 15 μl, preferably less than 5 μl and more preferably less than 1 μl.

Thus provision is made in this first concept for the second subordinate device, which is intended for reuse and therefore contains the pump, to have an outlet valve, which preferably opens depending on medium pressure and which is located so close to an interface to the second subordinate device that any possibly contaminated medium disposed in an outlet-duct portion of the first subordinate device and/or the second subordinate device on the other side of the outlet valve is not more than 15 μl. For the purposes of this invention, the term "outlet duct" refers to that portion of the path traversed by the liquid from the pump to the first discharge orifice which is filled, during the use of the discharging unit, with a continuous volume of flowing liquid consisting of the liquid medium only. The end of the outlet duct can be defined, for example, by that portion of a turbulence generating device, at which the liquid is no longer present in the form of a continuous volume of flowing liquid but instead exists in a nebulized form, in particular, consisting of small droplets.

Thus the distinctive feature of this first concept of the invention consists in the fact that the outlet valve, which following a discharging operation separates the potentially contaminated portion of the medium from that portion of the medium which is definitely not contaminated is disposed directly upstream of the interface between the subordinate devices. Embodiments are feasible in which the outlet duct ends in the region of the second subordinate device as defined above, and in which the outlet duct extends to as far as the interior of the first subordinate device. In the former embodiment, the discharge orifice is provided on the first subordinate device on the other side of a turbulence generating device disposed on the second subordinate device, and the medium passes through the discharge orifice in a nebulized form when the discharging unit is used according to specifications.

In a second concept of the invention, a generic discharging unit is developed in that the first discharge orifice, at least a portion of the outlet duct, and a first turbulence generating device provided in the outlet duct are part of a first subordinate device, and the pump and at least a portion of the outlet duct are part of a second subordinate device. The first subordinate device is one that can be coupled to the second subordinate device and likewise decoupled from the same without the use of tools. Furthermore, an internal volume of that portion of the outlet duct which is provided in the first subordinate device is less than 15 µl, preferably less than 5 µl and more preferably less than 1 µl.

Thus the distinctive feature of this second concept consists in the fact that the first subordinate device, which is not intended for reuse, comprises the first turbulence generating device, at which the medium is no longer expelled in the form of a continuous volume of flowing liquid. It has been found that the turbulence generating device offers very good protection of the discharging unit from contamination. Even if contamination of the turbulence generating device should occur due to use on an infected patient, such contamination does not usually spread to the interior of that portion of the outlet duct upstream of the turbulence generating device which is part of the first subordinate device. This portion of the outlet duct in the first subordinate device and the medium still located therein following a discharging operation are an effective barrier that prevents the contamination from spreading to the second subordinate device of the discharging unit. Therefore, it can be very advantageous to keep down the internal volume of that portion of the outlet duct which is provided in the first subordinate device such that it is in the range of from approximately 3 µl to 5 µl, so that the above barrier function is reliably achieved.

In order to achieve a high level of safety, provision can be additionally made for the first subordinate device to comprise a valve that opens preferably depending on medium pressure and that then also prevents contamination of the second subordinate device when the subordinate devices remain in the coupled state for a relatively long period of time following a discharging operation involving contamination of the first subordinate device.

For the purposes of this invention, the term "turbulence generating device" refers to a device that is supplied with medium in the outlet duct and that transforms the medium from a continuous volume of flowing liquid to a dischargeable form, more particularly a spray jet. Specifically, such a turbulence generating device can comprise inclined turbulence generating surfaces that cause the liquid to spin arcuately relatively to an axis defined by the central discharging direction, and this spinning of the liquid results in the formation of a conical spray jet.

For the purposes of the above concepts, the term "coupling and decoupling that can be executed without the use of tools" refers to the possibility of disconnecting and connecting the subordinate devices without the use of aids that are more than just human hands. This can also include a process of releasing locking means such as snap-on means that must be carried out beforehand if it is possible to carry out this releasing process solely by the application of force to accessible surfaces of the discharging unit. It is regarded as being very advantageous when disconnecting and connecting the subordinate devices is possible solely by the application of force to the subordinate devices relatively to each other in a disconnecting and connecting direction, and coupling is preferably achieved entirely without undercuts.

The possibility of handling the subordinate devices without the use of tools is necessary in order to enable the end user, for example the patient or a doctor performing a mass inoculation, to prepare the discharging unit for the next patient in a short period of time. Awkward disconnection of the subordinate devices by means of an additional tool is inacceptable in the case of mass inoculations, during which sometimes thousands of patients have to be inoculated.

It is regarded as being very advantageous to use the above two concepts for discharging units comprising nasal applicators, in which the first subordinate device comprises an applicator which is preferably in the form of a nasal tube and in which the first discharge orifice is provided.

It is of particular advantage when the second subordinate device that is reused according to specifications comprises an applicator that is more particularly in the form of a nasal tube and that comprises a second discharge orifice, while the first subordinate device is configured to be fitted onto this applicator of the second subordinate device. In such an embodiment, the second subordinate device of the discharging unit can also be used without the first subordinate device, since it already contains an applicator. This applicator is used for fixing the first subordinate device, when the discharging unit is used with the first subordinate device, in that the first subordinate device comprises contact surfaces which are intended for fixing said first subordinate device, preferably positively, to the second subordinate device and which are configured to match the shape of the applicator of the second subordinate device.

It is further advantageous when the second subordinate device comprises a second turbulence generating device disposed upstream of the second discharge orifice. This second turbulence generating device serves its intended purpose when the second subordinate device is used without the first subordinate device as a substantially generic discharging unit. However, when the first subordinate device is coupled to the second subordinate device as described above, the second turbulence generating device fails its intended purpose and acts merely as part of the outlet duct.

In a development of the invention, in which the first and the second subordinate devices each comprise a nasal tube, these nasal tubes have geometries that differ from each other. The “geometry of the nasal tube” refers to the external shape of the same, that is to say, the shape of all components of the nasal tube that come into contact with the nose of the patient according to specifications. A discharging unit of the invention can be adapted to suit various groups of patients, specifically adults, on the one hand, and children, on the other, by means of the configuration of the nasal tube with different geometries. Similarly, it is regarded as being advantageous when discharging units, in which the first and the second subordinate devices each comprise a turbulence generating device, have different turbulence generating devices that are each configured to generate different spraying properties. The difference in the spraying properties relates particularly to the acceptance angle of the conical portion of the spray jet and/or the size of the droplets produced by the turbulence generating device. Here again, the turbulence generating devices can be adapted particularly to meet specific requirements of adult patients, on the one hand, and children, on the other.

Furthermore, it is regarded as being particularly advantageous when the first subordinate device comprises a cap-like first external member and an internal member that can be inserted into said external member. This makes it easy to fabricate more complex structures within the first subordinate device. More particularly, the internal member can at least partially form the first turbulence generating device. Alternatively or additionally, the internal member can provide a sealing surface that bears against an external surface of the second subordinate device in the coupled state of the subordinate devices. It is advantageous, particularly as regards such a sealing surface, when the internal member is made of a more flexible material than the external member.

In a particularly preferred embodiment of the invention, the first and second subordinate devices are each provided with sealing surfaces that bear against each other in the coupled state of the subordinate devices and thus jointly seal the outlet duct in the transition region between the subordinate devices from the environment. It is of particular advantage when a median normal vector to these sealing surfaces forms an angle of less than 60°, preferably less than 30° and more preferably less than 15°, with the decoupling direction of the subordinate devices. Since the subordinate devices are preferably largely made of plastics components that deform readily when the subordinate devices are coupled, such a comparatively acute angle between the normal vector and the decoupling direction serves to prevent negative pressure from developing between the subordinate devices when the latter are decoupled, which negative pressure might cause contaminated medium to be drawn from the first subordinate device and be deposited on the external surfaces of the second subordinate device.

In a discharging unit of the invention, the second subordinate device preferably comprises two assemblies that can be moved relatively to each other in a pumping direction and that each comprise components of the pump such that a pumping operation can be achieved by causing relative displacement of these assemblies.

It is regarded as being particularly advantageous when the first subordinate device, that is to say, that component of the discharging unit which cannot be reused according to specifications, comprises a finger rest. An at least approximately flat surface that has a minimum size of 7 mm×7 mm and preferably a larger surface, is regarded as being such a finger rest, and a normal vector to this finger rest forms an angle of not more than 15° with the pumping direction. More particularly, the finger rest can be in the form of a bridge molded or coupled outwardly to the cap-like outer member of the first subordinate device. The embodiment of the first subordinate device comprising such a finger rest offers the advantage that the subordinate devices are also pressed against each other at the same time as the pumping operation of the discharging unit so that a reliable seal is ensured between the subordinate devices. In spite of the presence of such a finger rest on the first subordinate device, embodiments that also provide a finger rest on the second subordinate device are also advantageous, and this finger rest serves to make it possible to use the second subordinate device without the first subordinate device.

Furthermore, it is regarded as being advantageous when a discharging unit of the invention is provided with an additional first subordinate device, that is to say, when the discharging unit is in the form of a set consisting of a second subordinate device and at least two first subordinate devices. Thus the discharging unit includes all components that are required for use on a number of patients. In this case, it is particularly advantageous when the different first subordinate devices that are part of such a set differ from each other in terms of the geometry of the respective nasal tubes and/or the design of the first turbulence generating devices so that the discharging unit can be adapted to meet specific requirements, more particularly the specific requirements of adults as against those of children.

The invention further relates to a set comprising a discharging unit for discharging pharmaceutical media from a medium storage receptacle, in particular, a discharging unit of the type described above comprising a discharge orifice, a pump, and a first downwardly oriented connecting unit which serves to connect the discharging unit to a medium storage receptacle and which is in the form of a screw-threaded connecting unit particularly comprising a female screw thread, a snap-on connecting unit, or a plug-in connecting unit. The set further comprises an adapter unit having a second connecting unit which makes it possible to connect the adapter unit upwardly to the first connecting unit of the discharging unit, while as third connecting unit for connecting the adapter unit to a medium storage receptacle, and the second and third connecting units are joined to each other by means of a pipe segment. The first and third connecting units differ from each other.

Thus a set of such type comprises a discharging unit comprising a connecting unit provided for coupling the discharging unit to a defined type of medium storage receptacle. In particular, the connecting unit can comprise a screw thread for this purpose. It is also possible for the discharging unit to comprise first connecting units that are in the form of snap-on connecting units for snapping the discharging unit onto a medium storage receptacle, and plug-in connections provided for insertion into a complementary connecting unit on a medium storage receptacle with generation of compression in the radial direction.

In order to make it possible to connect this discharging unit to a medium storage receptacle for which it is not intended, according to specifications, there is included an adapter unit that can be connected by means of its second connecting unit to the first connecting unit of the discharging unit in place of the medium storage receptacle. For this purpose, the second connecting unit is shaped so as to complement the first connecting unit and is provided, for example and more particularly, with a male thread that mates with the female thread of the discharging unit. The second connecting unit is connected to the third connecting unit by means of a connecting pipe. The third connecting unit differs from the first connecting unit in such a manner that it permits the connection of the discharging unit to the medium storage receptacle, to which it would not have been possible to connect the first connecting unit. However, the basic design options of the third connecting unit are the same as those relevant to the first connecting unit.

Preferably, the first and second connecting units are designed such that they permit coupling to be carried out without the use of tools. It is possible, but not necessary, to provide the option of carrying out decoupling without the use of tools. In order to achieve a sufficiently good sealing effect at the transition between the first and second connecting units, on the one hand, and at the transition between the third connecting unit and the medium storage receptacle, on the other hand, there are preferably provided sealing elements that each extend along the periphery of the connecting units.

In order to make the adapter unit easier to handle, the adapter unit preferably comprises a radially outwardly oriented mounting element in the form of a mounting aid that extends outwardly in the radial direction above the third connecting unit. It is very advantageous when the mounting element is noncircular in shape about a principal axis defined by the second and third connecting units in order to enable the adapter unit to be screwed onto or into the discharging unit securely.

BRIEF DESCRIPTION OF THE DRAWINGS

Additional advantages and aspects of the invention are revealed in the claims and the following description of preferred exemplary embodiments of the invention that are explained below with reference to the figures, in which:

FIG. 1b shows a detail on an enlarged scale, FIG. 2b shows a detail on an enlarged scale.

DETAILED DESCRIPTION OF THE EXEMPLARY EMBODIMENTS

Figures 1A, 1B:
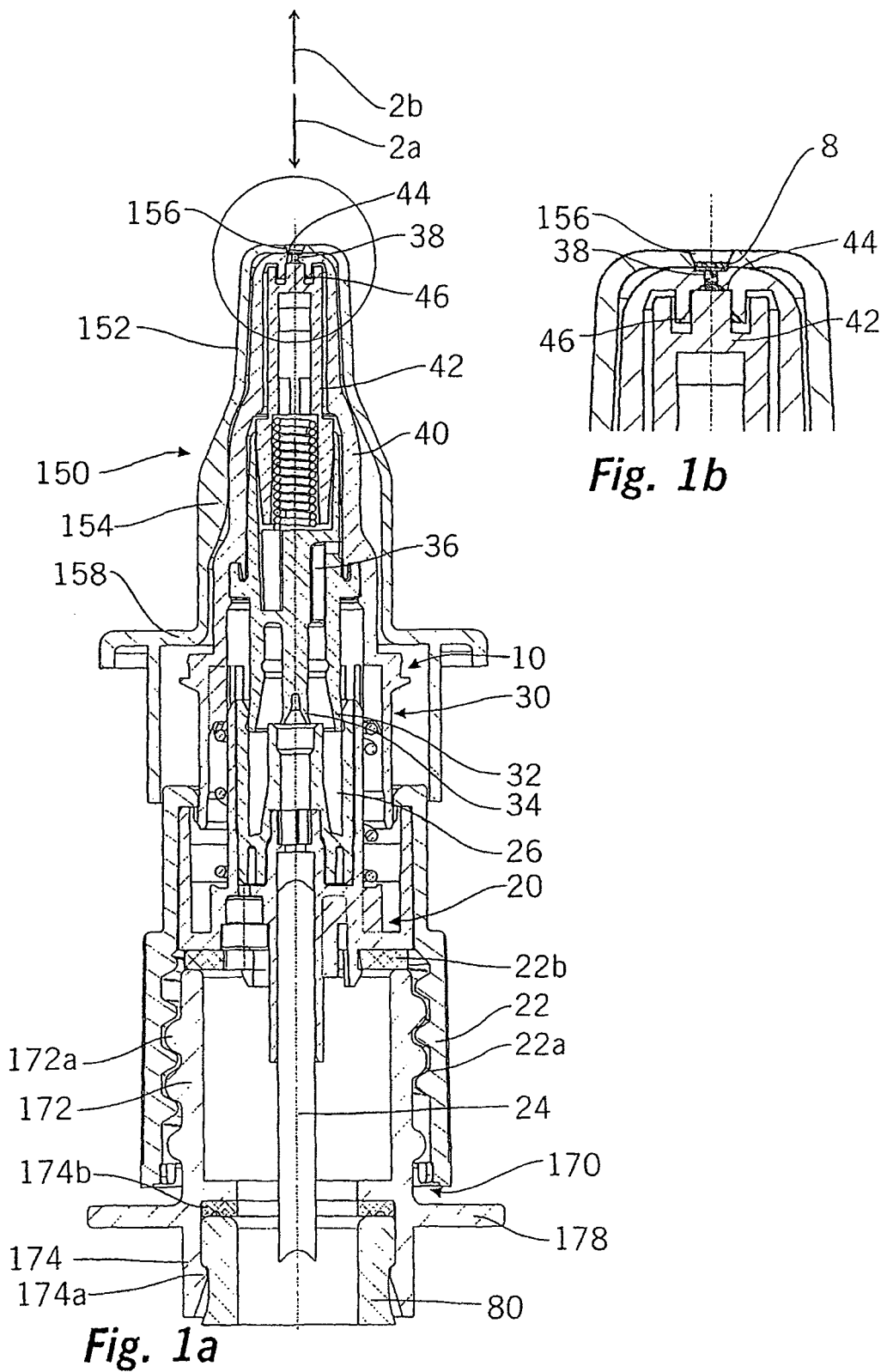
FIGS. 1a and 1b show a first discharging unit of the present invention comprising an adapter unit.

The two discharging units shown in FIGS. 1 and 2 both comprise the same three main components that are configured to be assembled by an end user, for example a doctor administering the medium capable of being discharged by the discharging unit. These three components consist of a basic unit 10 that is substantially identical in both of the embodiments shown in FIGS. 1 and 2 and represents the second subordinate device for the purposes of the present invention, a top attachment 150, 250 that represents the first subordinate device for the purposes of the present invention, and an adapter unit 170, 270.

Due to the fact that the design of the basic unit 10 is largely identical in each case, this component will now be explained first. The basic unit 10 comprises two assemblies 20, 30 that can be translatively displaced relatively to each other in a pumping direction 2a. The bottom assembly 20 comprises a connecting unit 22 provided with a female thread 22a and a resilient sealing ring 22b. An inlet duct 24 partially in the form of a standpipe passes through this connecting unit 22 and ends in a pump chamber 26 that is formed by portions of the lower assembly 20. Correspondingly, the upper assembly 30 comprises a piston 32 that extends into the pump chamber 26 and that, as a result of the relative displacement of the assemblies 20, 30, is capable of closing the inlet duct 24 by means of a closure element 34 in order to reduce the volume of the pump chamber 26 during continued relative displacement of the assemblies 20, 30, thus causing the discharging operation to take place. For this purpose, the upper assembly 30 is provided with a portion 36 of an outlet duct that leads to a discharge orifice 38 disposed at the distal end of a nasal tube 40. Provision is made inside the nasal tube 40 for a valve 42 that is pressed by spring force against the discharge orifice 38 and that opens the discharge orifice 38 only when there is sufficient medium pressure present in the outlet duct 36. As a counterpart to the valve gate 40, there is provided a sealing surface 44 on the internal surface of the nasal tube 40 so as to surround the discharge orifice 38. Directly upstream of the outlet valve 42, 44 there is provided a turbulence generating device composed of inclined turbulence generating surfaces 46 that swirl the liquid flowing from the pump chamber 26 to the discharge orifice 38 when the valve 40, 42 is open, said swirling of the liquid causing the medium to form a conical spray jet as it passes through the discharge orifice 38.

The basic unit 10 described above is designed such that it can be screwed directly without the use of adapter units 170, 270 onto a bottle of medium provided for this purpose. Furthermore, the basic unit is configured to be used without a top attachment 150, 250 forming a nasal dispenser.

The top attachments 150, 250 are provided to make it possible to make use of the basic unit 10 also and especially in the form of a discharging unit for mass inoculations.

The discharging unit shown in FIGS. 1a and 1b illustrates a first concept. The top attachment 150 is configured to be fitted onto the nasal tube 40. While the shape of the top attachment in the top region thereof is that of a nasal tube 152, its internal surface is provided with ribs 154 to ensure that the top attachment 150 is properly secured after it has been fitted onto the nasal tube 40. At its distal end, the top attachment 150 comprises a discharge orifice 156 that is larger than the discharge orifice 38 of the basic unit 10. A finger rest 158 extending radially outwardly is provided at the bottom end of the top attachment 150.

After this top attachment 150 has been fitted to the nasal tube 40 of the basic unit 10, a discharging operation can be carried out by the application of force to the finger rest 158 acting downwardly in the pumping direction 2a, since this application of force causes the upper assembly 30 of the basic unit 10 to be displaced together with the top attachment 150 relatively to the bottom assembly 20 of the basic unit 10 so that the medium located in the pump chamber 26 is expelled from the same. The medium is forced into the outlet duct 36, where the fluid pressure increases until the outlet valve 40, 42 opens and the medium that is made to swirl by the turbulence generating surfaces 46 is discharged through the discharge orifices 38, 156 in the form of a spray jet.

The application of force to the finger rest 158 not only enables the discharging operation described above to be achieved, but also ensures that the top attachment 150 is at the same time pressed against the nasal tube 40 of the basic unit 10 so that no medium will be lost between the top attachment 150 and the external surface of the nasal tube 40.

On completion of the discharging operation, the top attachment 150 can easily be pulled upwardly off from the basic unit 10 in the opposite direction 2b so that any potentially contaminated surfaces of the top attachment 150 can be removed in this way. Some contamination can still remain in the region of the discharge orifice 38 of the basic unit 10 in the embodiment shown in FIGS. 1a and 1b. It is therefore preferred that the discharge orifice 38 be disinfected first, by means of a disinfectant liquid, before a new top attachment 150 is fitted onto the basic unit. In doing so, any residual medium in the region of the discharge orifice 38 is also removed. This residual medium represents a volumetrically negligible loss.

After a new top attachment 150 has been fitted onto the basic unit, the discharging unit can be used for a subsequent patient without any risk of cross-contamination, since all surfaces that might have been contaminated have been removed or disinfected. The surfaces 8 indicated by dots in FIG. 1b show how small the amount of medium is that is lost when the top attachment 150 is replaced and the basic unit 10 is disinfected, if necessary. In the embodiment shown in FIGS. 1a and 1b, the medium lost is less than 0.1 µl. Since the medium in the outlet duct 36 would not be affected by any contamination and therefore need not be removed, medium can be discharged immediately after the replacement of the top attachment 150 without the need for further priming.

Figure 2B:
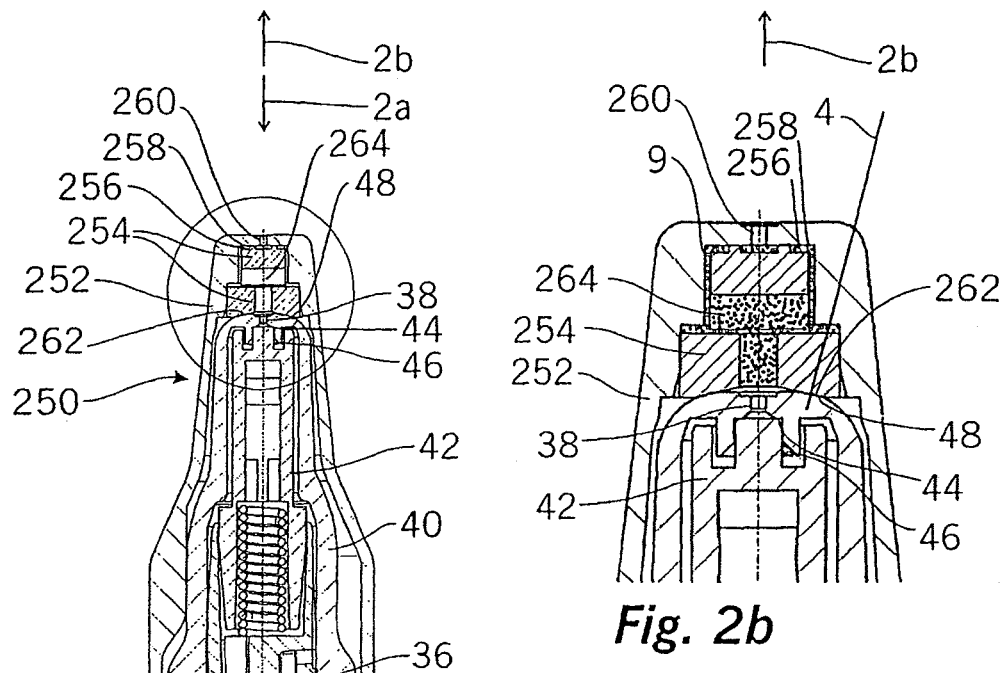
FIGS. 2a and 2b show a second discharging unit of the present invention comprising an adapter unit.
Figure 2A:
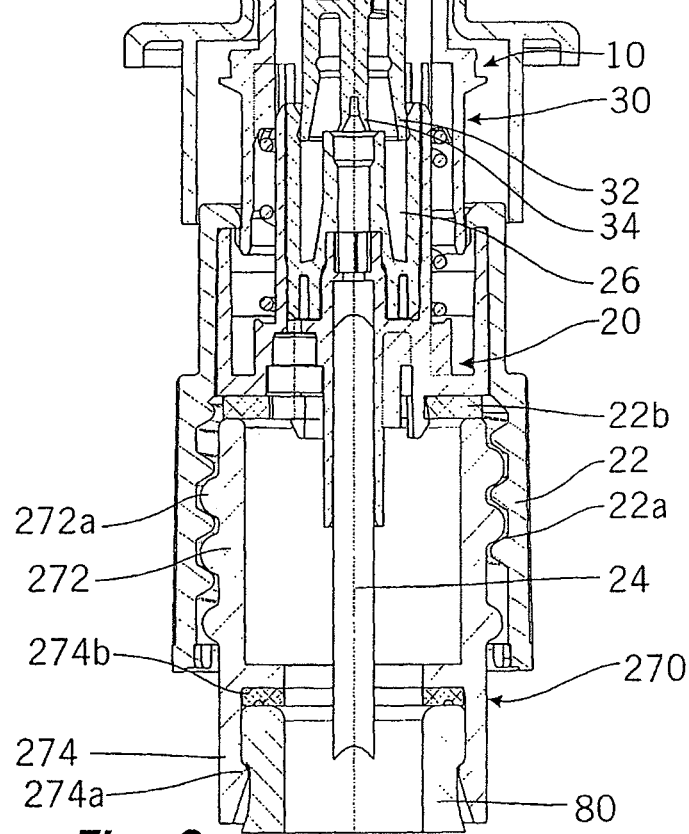

The top attachment 250 of the embodiment shown in FIGS. 2a and 2b has a more complex design that differs from that of the top attachment 150. As can be seen, in particular, in FIG. 2b, this second top attachment has a cap-like assembly 252, into which a one-piece component 254 of flexible plastics material is pressed. The top end face 256 of the inner assembly forms, together with the internal surface 258 of the cap-like outer assembly 252, a turbulence generating device that is disposed directly upstream of a discharge orifice 260. In a manner not shown in detail, this turbulence generating device also comprises inclined turbulence generating surfaces that cause the medium flowing past to swirl. The inner assembly 254 comprises a sealing surface 262 on the opposite side oriented toward the nasal tube 40 of the basic unit 10, which sealing surface 262 bears against a sealing-surface portion 48 of the basic unit 10 to form a seal in the coupled state, as shown in FIGS. 2a and 2b.

As described with reference to FIGS. 1a and 1b, the basic unit 10 of the discharging unit shown in FIGS. 2a and 2b is also operable when used separately. But when the basic unit 10 is used with the top attachment 250, the medium does not form a spray jet after flowing though the discharge orifice 38, but it is conveyed further in the form of a continuous stream of liquid along the top-attachment duct 264 as far as the turbulence generating device 256, 258. Here, the liquid stream is again made to swirl by the turbulence generating device 256, 258, as a result of which the medium is discharged to the environment through the discharge orifice 260 in the form of a conical spray jet.

The turbulence generating device 46 can alternatively be omitted, since it is not required when the basic unit 10 is used together with the top attachment 250. In this case, the basic unit 10 can be used only in combination with the top attachment 250.

Any contamination caused by a patient using the discharging unit shown in FIGS. 2a and 2b takes place primarily on the external surface of the cap-like outer member 252. It has been found that contamination spreads only in very rare cases as far as the turbulence generating device 256, 258. Even if this should happen, this contamination is additionally separated from the basic unit 10 by the liquid disposed in the top-attachment duct 264, so that any contamination does not by any means reach as far as the external surface of the nasal tube 40 of the basic unit 10.

Following the use of the basic unit 10 together with the top attachment 250 for the administration of an inoculant to a first patient, the top attachment 250 can be replaced for a second patient, as also in the case of the first embodiment shown in FIGS. 1a and 1b. Only the internal volume 9 of medium indicated by dots in FIG. 2b is lost in the process. The amount of this lost liquid ranges from only 3 to 5 μl. Disinfection of the nasal tube 40 of the basic unit 10 is not usually necessary, since any possible contamination will not spread to the nasal tube 40. This effect is also achieved by virtue of the fact that the sealing surfaces 262, 48 have a normal vector 4 that forms an angle of less than 30° with the decoupling direction 2*b*, so that negative pressure will not develop between the top attachment 250 and the basic unit 10 when the top attachment 250 is decoupled from the latter. Such negative pressure might have caused contaminated medium to be drawn up to the nasal tube 40. Instead, there is direct loss of contact between the sealing surfaces 48, 262 when the top attachment is decoupled from the basic unit.

Both of the discharging devices shown in FIGS. 1 and 2 comprise an adapter unit 170, 270. The adapter units comprise, at their top ends, a second connecting unit 172, 272 that is provided with a male screw thread 172*a*, 272*a*. This male screw thread 172*a*, 272*a* is adapted to mate with the female screw thread 22*a* on the first connecting unit 22 of the basic unit 10. At their opposing bottom ends, the adapter units 170, 270 each comprise a third connecting unit 174, 274 which is cylindrical in shape and on the internal surface of which there is provided a snap-on edge 174*a*, 274*a* that serves the purpose of being fitted onto a medium storage receptacle 80 that does not have a screw-threaded connecting unit but has a snap lock complementary to the third connecting unit 174, 274. For the purpose of achieving a full seal, the third connecting units 174, 274 are each equipped with a resilient sealing element 174*b*, 274*b* that extends along the periphery of the connecting units.

The adapter units 170, 270 that are included together with the basic unit 10 allow the basic unit 10, which is originally not configured to be connected to a medium storage receptacle of the type of the medium storage receptacle 80, to be connected indirectly, by way of the adapter units 170, 270, to such a medium storage receptacle 80. As a result, this makes shorter reaction times possible when it is required to supply the market with a plurality of discharging units for medium storage receptacles of the type of the medium storage receptacle 80, since the basic unit 10 and the top attachments 150, 250 may already have been prefabricated in large quantities and can thus be supplemented with simply and rapidly producible adapter units 170, 270 should it be required to connect the basic unit to a medium storage receptacle of the type of the medium storage receptacle 80.

The adapter units 170, 270 differ from each other only in that the adapter unit 170 of the discharging unit shown in FIG. 1*a* comprises a mounting element 178 that is in the form of an externally molded radial surface and that facilitates the process of snapping the third connecting unit 174 onto the medium storage receptacle 80 and coupling the second connecting unit 172 to the first connecting unit 22.

The invention claimed is:

1. A discharging unit set for discharging pharmaceutical media from a medium storage receptacle, comprising:
- at least two first subordinate devices;
- a second subordinate device configured to be sequentially connected to one of said first subordinate devices to form a discharging unit;
- a pump;
- a first discharge orifice; and
- an inlet duct for connecting said medium storage receptacle to said pump, and an outlet duct for connecting said pump to said first discharge orifice;
- wherein each of said first subordinate devices includes the first discharge orifice;
- wherein said second subordinate device includes said pump, at least a first portion of said outlet duct and an outlet valve provided in said outlet duct; and
- wherein each of said first subordinate devices is individually capable, without use of tools, of being coupled to, or decoupled from, said second subordinate device and wherein an internal volume of said outlet duct extending from said outlet valve to said first discharge orifice is less than 15 μl.

2. The discharging unit set as defined in claim 1, wherein:
- each of said first subordinate devices includes at least a second portion of said outlet duct, and a first turbulence generating device provided in said outlet duct; and
- the internal volume of said outlet duct provided in said first subordinate device is less than 15 μl.

3. The discharging unit set as defined in claim 1, wherein each of said first subordinate devices has an applicator and said first discharge orifice is provided in said applicator.

4. The discharging unit set as defined in claim 1, wherein:
- said second subordinate device has an applicator; and
- each of said first subordinate devices is designed to be placed on said applicator of said second subordinate device.

5. The discharging unit set as defined in claim 4, wherein said second subordinate device has a second discharge orifice located upstream of a turbulence generating device.

6. The discharging unit set as defined in claim 4, wherein:
- said first subordinate devices and said second subordinate device each have a nasal tube and the nasal tubes have geometries deviating from each other; and/or
- said first subordinate devices and said second subordinate device each have a turbulence generating device and the turbulence generating devices are designed to produce different spraying properties.

7. The discharging unit set as defined in claim 1, wherein:
- each of said first subordinate devices has a cap-like first external housing and an internal member inserted therein; and the internal member
forms at least partially a first turbulence generating device and/or
provides a sealing surface which in a coupled state bears against an external surface of said second subordinate device.

8. The discharging device set as defined in claim 1, wherein:
said first subordinate devices and said second subordinate device each include a sealing surface, with the sealing surfaces bearing against each other in a coupled state of one of said first subordinate devices and said second subordinate device to seal the outlet duct from an outside environment, wherein a perpendicular vector relative to the sealing surfaces encloses with a decoupling device of said subordinate devices an angle of less than 60°.

9. The discharging unit set as defined in claim 1, wherein a finger rest is provided on each of said first subordinate devices.

10. The discharging unit set as dedfined in claim 1, wherein said first subordinate devices and said second subordinate device are each configured for purely friction-locked coupling.

11. The discharging unit set as defined in claim 1, wherein:
each of the first subordinate devices are differently configured as regards to a geometry of nasal tubes and/or a design of first turbulence generating devices.

12. The discharging unit set as defined in claim 1, further including:
a first downwardly directed connecting element for connecting said discharging unit to a medium storage receptacle;
wherein said first connecting element is a screw-threaded connecting unit; and
an adapter unit comprising a second connecting element for upwardly directed attachment to said first connecting element of said discharging unit and a third connecting element for connecting said adapter unit to the medium storage receptacle, the second connecting element being interconnected to the third connecting element via a pipe section;
wherein the first and third connecting elements differ from each other.

13. The discharging unit set as defined in claim 12 wherein:
said connecting elements of said adapter unit are coaxial with a principal axis; and
a radially outwardly directed mounting element is provided on said adapter unit and said mounting element is non-circular about said principal axis.

14. The discharging unit set as defined in claim 1, wherein the internal volume of said outlet duct extending from said outlet valve to said first discharge orifice is less than 5µl.

15. The discharging unit set as defined in claim 1, wherein the internal volume of said outlet duct extending from said outlet valve to said first discharge orifice is less than 1µl.

16. The discharging unit set as defined in claim 3, wherein said applicator is a nasal tube.

17. The discharging unit set as defined in claim 4, wherein said applicator is a nasal tube.

18. The discharging device set as defined in claim 8, wherein the perpendicular vector relative to the sealing surfaces encloses with the decoupling device of said subordinate devices an angle of less than 30°.

19. The discharging device set as defined in claim 18, wherein the perpendicular vector relative to the sealing surfaces encloses with the decoupling device of said subordinate devices an angle of less than 15°.

20. A discharging unit set for discharging pharmaceutical media from a medium storage receptacle, comprising:
a first subassembly including a pump for moving the media in the medium storage receptacle through the first subassembly from an inlet duct to an outlet duct, the first subassembly including the inlet duct and at least a portion of the outlet duct, the first subassembly including an outlet valve in the outlet duct; and
at least two second subassemblies, with each of the second subassemblies being configured to be individually connected to the first subassembly for forming a discharging unit, each of the second subassemblies including a discharge orifice that is aligned with the outlet duct of the first subassembly when connected to the first subassembly;
wherein each of the second subassemblies is individually capable, without use of tools, of being sequentially coupled to, or decoupled from, the first subassembly and wherein an internal volume of the outlet duct extending from the outlet valve to the discharge orifice is less than 15 µl.

21. The discharging device set as defined in claim 20, wherein:
the first subassembly and each of the second subassemblies include a sealing surface, with the sealing surfaces bearing against each other in a coupled state of the first subassembly and one of the second subassemblies to seal the outlet duct from an outside environment, wherein a perpendicular vector relative to the sealing surfaces encloses with a decoupling device of said subassemblies an angle of less than 60°.

22. The discharging unit set as defined in claim 20, wherein a finger rest is provided on each of the second subassemblies.

23. The discharging unit set as defined in claim 20, wherein the first subassembly and each of the second subassemblies are configured for purely friction-locked coupling.

* * * * *